US007087575B2

(12) United States Patent
Richelson et al.

(10) Patent No.: US 7,087,575 B2
(45) Date of Patent: Aug. 8, 2006

(54) TREATING THE EFFECT OF NICOTINE

(75) Inventors: Elliott Richelson, Ponte Vedra Beach, FL (US); Paul Fredrickson, Jacksonville, FL (US); Mona Boules, Jacksonville, FL (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 257 days.

(21) Appl. No.: 10/198,697

(22) Filed: Jul. 18, 2002

(65) Prior Publication Data
US 2004/0014651 A1 Jan. 22, 2004

(51) Int. Cl.
*C12Q 1/37* (2006.01)
*A61K 38/00* (2006.01)
*A61K 38/04* (2006.01)
*A01K 37/18* (2006.01)

(52) U.S. Cl. .............................. 514/14; 435/23; 514/2; 514/813; 530/300; 530/327
(58) Field of Classification Search .................. 435/23; 514/2, 14, 813; 530/300, 327
See application file for complete search history.

(56) References Cited

U.S. PATENT DOCUMENTS

| 4,299,838 A | 11/1981 | Durlach |
| 4,331,646 A | 5/1982 | Delaage |
| 4,518,587 A | 5/1985 | Laruelle et al. |
| 5,393,740 A | 2/1995 | Amagaya et al. |
| 5,631,265 A | 5/1997 | Audia et al. |
| 6,046,180 A | 4/2000 | Jackson et al. |
| 6,214,790 B1 * | 4/2001 | Richelson et al. .............. 514/2 |

FOREIGN PATENT DOCUMENTS

| EP | 0 333 071 A2 | 9/1989 |
| WO | WO 96/03400 | 2/1996 |
| WO | WO 97/39162 | 12/1996 |
| WO | WO 97/48400 | 12/1997 |
| WO | WO 99/52539 | 10/1999 |

OTHER PUBLICATIONS

Imperato et al. European Journal of Pharmacology, 1986, vol. 132, pp. 337-338.*
Hurt et al. The new England Journal of Medicine, 1997, vol. 337, vol. 337(17), pp. 1195-1202.*
Al-Rodhan et al., "Structure-antinociceptive activity of neurotensin and some novel analogues in the periaqueductal gray region of the brainstem," *Brain Res.*, 1991, 557:227-235.

Benowitz, "Pharmacodynamics of nicotine: implications for rational treatment of nicotine addiction," *Br. J. Addiction*, 1991, 86:495-499.
Bissette et al., "Hypothermia and intolerance to cold induced by intracisternal administration of the hypothalamic peptide neurotensin," *Nature*, 1976, 262:607-609.
Boules et al., "A novel neurotensin peptide analog given extracranially decreases food intake and weight in rodents," *Brain Res.*, 2000, 865:35-44.
Boules et al., "Neurotensin analog selective for hypothermia over antinociceptiom and exhibiting atypical neuroleptic-like properties,"*Brain Res.*, 2001, 919:1-11.
Boules et al., "A novel neurotensin analog blocks cocaine- and D-amphetamine-induced hyperactivity," *Eur. J. Pharmacol.*, 2001, 426:73-76.
Boules et al., "Antiparkinson-like effects of a novel neurotensin analog in unilaterally 6-hydroxydopamine lesioned rats," *Eur. J. Pharmacol.*, 2001, 428:227-233.
Bowden et al., "Dopamine $D_1$ and $D_2$ receptor binding sites in brain samples from depressed suicides and controls," *Brain Res.*, 1997, 752:227-233.
Carraway and Leeman, "The Isolation of a New Hyprotensive Peptide, Neurotensin, from Bovine Hypothalami," *J. Biol. Chem.*, 248(19):6854-6861.
Clineschmidt and McGuffin, "Neurotensin Administered Intracisternally Inhibits Responsiveness of Mice to Noxious Stimuli," *Eur. J. Pharmcol.*, 1977, 46:395-396.
Cusack et al., "Pharmacological Studies on Novel Neurotensin Mimetics: Discovery of a Pharmacologically Unique Agent Exhibiting Concentration-Dependent Dual Effects as Antagonist and Agonist," *Mol. Pharmacol.*, 1993, 44:1036-1040.
Cusack et al., "Pharmacolgical and Biochemical Profiles of Unique Neurotensin 8-13 Analogs Exhibiting Species Selectivity, Stereoselectivity, and Superagonsim," *J. Biol. Chem.*, 1995, 270(31): 18359-18366.

(Continued)

*Primary Examiner*—Janet L. Andres
*Assistant Examiner*—Joyce Tung
(74) *Attorney, Agent, or Firm*—Fish & Richardson P.C.

(57) ABSTRACT

The invention provides methods and materials for treating the effects of nicotine. In particular, the invention provides methods that involve administering a neurotensin receptor (NTR) agonist to a mammal that has been exposed to nicotine. The NTR agonist typically is administered in an amount effective to diminish or abolish the effects that nicotine has on the treated mammal. NTR agonists that can be used in methods of the invention include neurotensin (NT) polypeptide analogs such as NT69L. The invention also provides compositions containing an NTR agonist in combination with other agents used to help overcome nicotine effects such as sensitization and dependence. The compositions provided herein can be used to treat the effects of nicotine, including hyperactivity, hypothermia, respiratory distress, and hypertension.

3 Claims, 7 Drawing Sheets

OTHER PUBLICATIONS

Cusack et al., "Reversal of Haloperidol Induced Catalepsy in Rats by a Neurotensin Agonist," *Biol. Psychiatry*, 1999, 45:88S, Abstract No. 288.

Cusack et al., "Effects of a novel neurotensin peptide analog given extracranially on CNS behaviors mediated by apomorphine and haloperidol," *Brain Res.*, Abstracts and Proceedings of the 2nd Brain Research Interactive Symposium, Miami, FL, Oct. 21-23, 1999, Abstract No. P3-22.

Cusack et al., "A Single Amino Acid of the Human and Rat Neurotensin Receptors (Subtype 1) Determining the Pharmacological Profile of a Species-Selective Neurotensin Agonist," *Biochem. Pharmacol.*, 2000, 60:793-801.

Cusack et al., "Analysis of binding sites and efficacy of a species-specific peptide at rat and human neurotensin receptors," *J. Peptide Res.*, 2000, 55:72-80.

Fauq et al., "Synthesis of (2S)-2-amino-3-(1H-4-indolyl)propanoic acid, a novel tryptophan analog for structural modification of bioactive peptides," *Tetrahedron: Asymmetry*, 1998, 9:4127-4134.

Fiore et al., "Helping Wisconsin Women Quit Smoking: A Successful Collaboration," *Wisconsin Medical Journal*, Apr. 2000, 99:68-72.

Fredrickson et al., "Blockade of Nicotine-Induced Locomotor Sensitization by a Novel neurotensin Analog in Rats," *Society for Research on Nicotine and Tobacco*, 8th Annual Meeting, Feb. 20-23, 2002, Savannah, Georgia, Abstract No. RP-2.

Fredrickson et al., "Novel Neurotensin Analog Blocks Nicotine-Induced Locomotor Sensitization," *Fourth European Conference of the Society for Research on Nicotine and Tobacco—"Improving Knowledge and Treatments pf Nicotine Addiction,"* Santander, Spain, Oct. 3-5, 2002, Abstract No. 58.

Fredrickson et al., "Blockade of nicotine-induced locomotor sensitization by a novel neurotensin analog in rats," *Eur. J. Pharmacol.*, 2003, 458:111-118.

Griffith et al., "Induction of Brain Hypothermia by a Neurotensin Analog in Awake Rats," AHA Stroke Meeting Poster, (Abstract only).

Hedley et al., "The Neurotensin Agonsit NT69L Reverses Dizocilpine-Induced Disruption of Prepulse Inhibition in the Rat," *Society for Neuroscience*, 2002, (Abstract only).

Henningfield et al., "Cigarette Smokers Self-Administer Intravenous Nicotine," *Pharmacol. Biochem. Behav.*, 1983, 19:887-890.

Hertel et al., "Repeated administration of the neurotensin analogue NT69L on amphetamine-induced hyperactivity," *Eur. J. Pharmacol.*, 2001, 422:77-81.

Hertel et al., "Repeated adminstration of the neurotensin analogue NT69L induces tolerance to its suppressant effect on conditioned avoidance behaviour," *Eur. J. Pharmacol.*, 2002, 439:107-111.

Huang and Hanson, "Differntial effect of haloperidol on release of neurotensin in extrapyramidal and limbic systems," *Eur. J. Pharmacol.*, 1997, 332:15-21.

Hughes et al., "Are higher doses of nicotine replacement more effective for smoking cessation?" *Nicotine Tobacco Research*, 1999, 1:169-174.

Jolicocur and Barbeau, "Differential Neurobehavioral Effects of Neurotensin and Structural Analogues," *Peptides*, 1981, 2:171-175.

Katz et al., "Neurotensin Analog NT69L Induces Rapid and Prolonged Hypothermia after Hypoxic Ischemia," *Academic Emergency Medicine*, 2001, 8(12):1115-1121.

Kilts et al., "Simultaneous Quantification of Dopamine, 5-Hydroxytryptamine and Four Metabolically Related Compounds by Means of Reversed-Phase High-Performance Liquid Chromatography with Electrochemical Detection," *J. Chromotography*, 1981, 225:347-357.

Kitabgi et al., "Neurotensin Binding to Extraneural and Neural Receptors: Comparison with Biological Activity and Structure-Activity Relationships," *Mol. Pharmacol.*, 1980, 18:11-19.

Krstulovic, "Investigations of Catecholamine Metabolism Using High-Performance Liquid Chromatography," *J. Chromatogr.*, 1982, 229:1-34.

Lambert et al., "Anatomy and Mechanisms of Neurotensin-Dopamine Interactions in the Central Nervous System," *Ann. N.Y. Acad. Sci.*, 1995, 757:377-389.

Li et al., "Neurotensin peptides antagonistically regulate postynapic dopamine $D_2$ receptors in rat nucleus accumbens: a receptor binding and microdialyis study," *J. Neural Transm. [Gen Sect]*, 1995, 102:125-137.

McMahon et al., "Neurotensin analogs, Indications for use as potential antipsychotic compounds," *Life Sciences*, 2002, 70:1101-1119.

Morbeck et al., "Analysis if Hormone-Receptor Interaction Sites Using Synthetic Peptides: Receptor Binding Regions of the α-Subunit fo Human Choriogonadotropin," *Methods: A Companion to Methods in Enzymology*, 1993, 5:191-200.

*Morbidity and Mortality Weekly Report*, 2000, 49(RR-16):1-27.

Pabreza et al., "[$^3$H]Cystine Binding to Nicotine Cholinergic Receptors in Brain," *Mol. Pharmacol.*, 1991, 39:9-12.

Radke et al., "A Typical Antipsychotic drugs selectively increase neurotensins efflux dopamine termina regions," *Proc. Natl. Acad. Sci. USA*, 1998, 95:11462-11464.

Rennard and Daughton, "Smoking Cesation," *Chest*, 2000, 117(5, Suppl. 2):360S-364S (printed from the internet, 9 ps.).

Richelson et al., "Novel Neurotensin Peptide Analogs That Cross the Blood-Brain Barrier as Possible Antipsychotic Drugs: Preclinical Studies," *Int. J. Neuropsychopharmacol.*, 2000, 3(Suppl. 1):S374, Abstract No. P. 19.30.

Richelson et al., "Effects of a novel neurotensin peptide analog given extracranially on CNS behaviors mediated by apomorphine and haloperidol," *Movement Disorders*, 2000, 15(Suppl. 3):107, Abstract No. P580.

Richelson et al., "A Brain-Penetrating Neurotensin Analog Blocks the Supersensitivity to Apormorphine in an Animal Model of Parkinson's Disease (PD)," *World J. Biol. Psychiatry*, 2001, vol. 2, Suppl. 1, Abstract No. O003-07.

Richelson et al., "A Brain-Penetrating Neurotensin Analog Blocks the Supersensitivity to Apomorphine in an Animal Model of Parkinson's," *National Institute of Mental Health*, NCDEU Poster Abstracts, Poster Session I-45, (printed from the Internet Jan. 28, 2003, 1 pg.).

Sarhan et al., "Comparative Antipsychotic Profiles of Neurotensin and a Related Systemically Active Peptide Agonist," *Peptides*, 1997, 18(8):1223-1227.

Snijders et al. "Neurotensin Induces Catalepsy in Mice," *Neuropharmacology*, 1982, 21:465-468.

Stolerman and Jarvis, "The scientific case that nicotine is addictive," *Psychopharmacology*, 1995, 117:2-10.

Troxler, "Präparative Verwendung von MANNICH-basen von Hydroxy-indolen als Alkylierungsmittel," *Helvetica Chimica Acta*, 1968, 51(6):1214-1224, (English summary only).

Tyler et al., "In vitro binding and CNS effects of novel neurotensin agonists that cross the blood-brain barrier," *Neuropharmacology*, 1999, 38:1027-1034.

Tyler-McMahon et al., "Highly potent neurotensin analog that causes hypothermia and antinociception," *Eur. J. Pharmacol.*, 2000, 390:107-111.

Tyler-McMahon et al., "Neurotensin: peptide for the next millennium," *Regulatory Peptides*, 2000, 93:125-136.

Vincent et al., "Neurotensin and neurotensin receptors," *TIPS*, 1999, 20:302-309.

* cited by examiner

SEQUENCE LISTING

```
<160> NUMBER OF SEQ ID NOS: 3
<210> SEQ ID NO 1
<211> LENGTH: 13
<212> TYPE: PRT
<213> ORGANISM: Homo sapiens

<400> SEQUENCE: 1

Glu Leu Tyr Glu Asn Lys Pro Arg Arg Pro Tyr Ile Leu
 1               5                  10

<210> SEQ ID NO 2
<211> LENGTH: 6
<212> TYPE: PRT
<213> ORGANISM: Homo sapiens

<400> SEQUENCE: 2

Arg Arg Pro Tyr Ile Leu
 1               5

<210> SEQ ID NO 3
<211> LENGTH: 6
<212> TYPE: PRT
<213> ORGANISM: Artificial Sequence
<220> FEATURE:
<223> OTHER INFORMATION: Synthetically generated polypeptide

<400> SEQUENCE: 3

Arg Lys Pro Trp Leu Leu
 1               5
```

TREATING THE EFFECT OF NICOTINE

TECHNICAL FIELD

This invention relates to methods and materials for treating the effects of nicotine.

BACKGROUND

Cigarette smoking is the single most preventable cause of morbidity and mortality in the United States, accounting for approximately 427,000 deaths each year [(2000) Morbidity and Mortality Weekly Report 49:1–27]. Nicotine is widely accepted as the tobacco substance that causes addiction [Benowitz (1991) Br. J Addict. 86:495–499; Henningfield et al. (1983) Pharmacol. Biochem. Behav. 19:887–890; and Stolerman and Jarvis (1995) Psychopharmacol. 117:2–10]. Current pharmacotherapies available for those attempting to quit smoking generally involve nicotine replacement and bupropion, which approximately doubles the cessation rate versus placebo [Hughes et al. (1999) Nicotine Tob. Res. 1: 169–174]. However, even with concomitant behavioral therapy, long-term success rates range from 25 to 45 percent [Fiore et al. (2000) WMJ 99:68–72]. New therapies are needed, particularly for those with psychiatric co-morbidity and for anyone failing existing therapies [Hughes et al. supra; Rennard and Daughton (2000) Chest 117:360S–364S].

SUMMARY

The invention provides methods and materials for treating the effects of nicotine. In particular, the invention provides methods that involve administering a neurotensin receptor (NTR) agonist to a mammal that has been exposed to nicotine. The NTR agonist typically is administered in an amount effective to diminish or abolish the effects that nicotine has on the treated mammal. NTR agonists that can be used in methods of the invention include neurotensin (NT) polypeptide analogs such as NT69L. The invention also provides compositions containing an NTR agonist in combination with other agents used to help overcome nicotine effects such as sensitization and dependence. The compositions provided herein can be used to treat the effects of nicotine, including hyperactivity, hypothermia, respiratory distress, and hypertension.

The invention is based on the discovery that administration of NTR agonists can reduce the effects of nicotine. For example, the invention is based on the discovery that NT69L can prevent nicotine-induced hyperactivity in animals that have not previously been exposed to nicotine. The invention also is based on the discovery that treatment with NT69L can reduce the effects of nicotine in animals previously exposed to nicotine.

The invention features a method for reducing a nicotine effect in a mammal pre-exposed to nicotine. The method can involve administering a neurotensin receptor agonist to the mammal in an amount effective to reduce the nicotine effect. The neurotensin receptor agonist can be a polypeptide. The polypeptide can contain an amino acid analog (e.g., L-neo-Trp). The polypeptide can be selected from the group consisting of NT(1–13), NT(8–13), NT69L, NT69L', and NT76. The administering can be by injection.

The invention also features a composition containing a neurotensin receptor agonist and a smoking cessation compound. The neurotensin receptor agonist can be a polypeptide selected from the group consisting of NT(1–13), NT(8–13), NT69L, NT69L', and NT76. The smoking cessation compound can be bupropion. The composition also can contain a pharmaceutically acceptable carrier.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
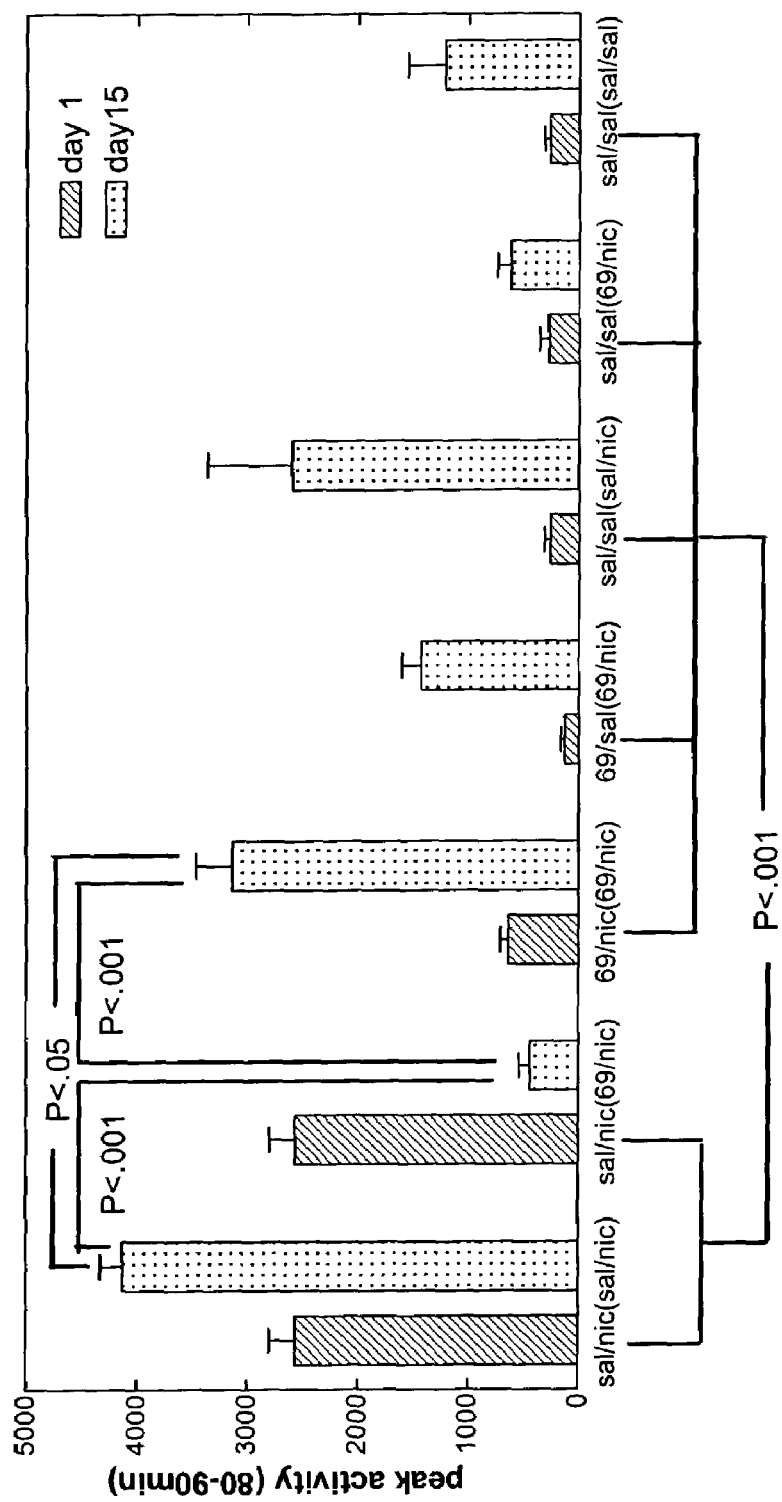
FIG. 1 is a bar graph showing the effect of NT69L on nicotine-induced locomotor activity in rats. Sal, saline; nic, nicotine; 69, NT69L.

The invention provides methods and materials for treating the effects of nicotine. In particular, the invention provides methods that involve administering an NTR agonist to a mammal such as a human that has been exposed to nicotine. The NTR agonist typically is administered in an amount effective to diminish or abolish the effects that nicotine has on the treated mammal.

"NTR agonist" as used herein refers to any molecule that binds to an NTR and induces an NTR response. NTR agonists include, without limitation, polypeptides and other agents such as small molecules. For example, an NTR agonist can be a polypeptide such as NT, NT(1–13), NT(8–13), and NT69L. Typically, NTR agonists induce NTR responses such as antinociception, hypothermia, diminished food consumption, blockade of muscle rigidity (catalepsy) caused by antipsychotic drugs (e.g., haloperidol), and inhibition of climbing behavior caused by the dopamine receptor agonist apomorphine. NTR responses can be measured using any method. For example, antinociception can be measured using pain tests such as tail flick and paw withdrawal studies. Briefly, tail flick and paw withdrawal studies typically involve subjecting an animal to a painful stimulus (e.g., heat, a pin prick, or a pinch on the foot), and measuring the length of time or amount of pinching force applied before the animal physically responds to the stimulus by flicking its tail or withdrawing its paw. NTR effects also can be measured in any suitable cell system. For example, NTR effects can be measured in human colonic adenoma cells (HT29 cells) by measuring the formation of second messengers (e.g., release of inositol phosphates or increase in intracellular levels of calcium ions). The specificity of NTR responses can be confirmed using NTR antagonists such as SR48692 and SR142948A.

NT is a tridecapeptide [Carraway and Leeman (1973) J. Biol. Chem. 248:6854–6861] that induces antinociception and hypothermia upon direct administration to brain. Systemic administration of NT does not induce these effects, however, since NT is rapidly degraded by proteases and has poor blood brain barrier permeability. NT behaves as a neurotransmitter or neuromodulator in the CNS, and there are striking interactions between NT (via its receptors) and central dopaminergic systems [Tyler-McMahon et al. (2000) Regul. Pept. 93:125–136; and Lambert et al. (1995) Ann. NY Acad. Sci. 757:377–389].

The complete amino acid sequence of NT(1–13) is pyro-Glu-Leu-Tyr-Glu-Asn-Lys-Pro-Arg -Arg-Pro-Tyr-Ile-Leu (SEQ ID NO:1). Most, if not all, of the activity mediated by NT(1–13) also can be seen with the shorter fragment, NT(8–13), which has the sequence Arg-Arg-Pro-Tyr-Ile-Leu (SEQ ID NO:2). These NT polypeptides, as well as other NTR agonists, can be used as described herein to reduce nicotine effects.

NTR agonists that can reduce the effects of nicotine include, without limitation, brain-penetrating analogs of NT polypeptides. Such polypeptides can have amino acid sequences that are based on the sequence of NT(8–13) and can incorporate one or more amino acid analogs such as D-or L-neo-tryptophan [Fauq et al. (1998) Tetrahedron: Assymetry 9:4127–4134]. Neo-tryptophan (2-amino-3-[1H-indolyl]propanoic acid) places the indole group of tryptophan in a unique orientation in terms of steric and electrostatic fields, such that polypeptides containing neo-tryptophan provide novel arrangements for side chain interactions. For example, the invention provides methods for using polypeptides having the amino acid sequence N-methyl-Arg -Lys-Pro-L-neo-Trp-tert-Leu-Leu (SEQ ID NO:3; referred to herein as NT69L). Examples of other polypeptides that are NT analogs are provided herein in Table 1.

TABLE I

Amino acid sequences of selected NTR agonists

| Polypeptide | 1 | 2 | 3 | 4 | 5 | 6 | 7 | 8 | 9 | 10 | 11 | 12 | 13 |
|---|---|---|---|---|---|---|---|---|---|---|---|---|---|
| NT | p-Glu | L-Leu | L-Tyr | L-Glu | L-Asn | L-Lys | L-Pro | L-Arg | L-Arg | L-Pro | L-Tyr | L-Ile | L-Leu |
| NT(8–13) | | | | | | | | L-Arg | L-Arg | L-Pro | L-Tyr | L-Ile | L-Leu |
| NT(9–13) | | | | | | | | | L-Arg | L-Pro | L-Tyr | L-Ile | L-Leu |
| NTW | | | | | | | | L-Arg | L-Arg | L-Pro | L-Trp | L-Ile | L-Leu |
| NT (tert-Leu) | | | | | | | | L-Arg | L-Arg | L-Pro | L-Tyr | tert-Leu | L-Leu |
| Eisai* | | | | | | | | N-methyl-Arg | L-Lys | L-Pro | L-Trp | tert-Leu | L-Leu |
| NT2 | | | | | | | | D-Lys | L-Arg | L-Pro | L-Tyr | L-Ile | L-Leu |
| NT24 "27" | | | | | | | | L-Arg | D-Orn$^&$ | L-Pro | L-Tyr | L-Ile | L-Leu |
| NT34 | | | | | | | | L-Arg | L-Arg | L-Pro | L-3,1'-Nal$^\#$ | L-Ile | L-Leu |
| NT64D | | | | | | | | L-Arg | L-Arg | L-Pro | D-neo-Trp | L-Ile | L-Leu |
| NT64L | | | | | | | | L-Arg | L-Arg | L-Pro | L-neo-Trp | L-Ile | L-Leu |
| NT65L | | | | | | | | L-Arg | L-Arg | L-Pro | L-neo-Trp | tert-Leu | L-Leu |
| NT66D | | | | | | | | D-Lys | L-Arg | L-Pro | D-neo-Trp | tert-Leu | L-Leu |
| NT66L | | | | | | | | D-Lys | L-Arg | L-Pro | L-neo-Trp | tert-Leu | L-Leu |
| NT67L | | | | | | | | D-Lys | L-Arg | L-Pro | L-neo-Trp | L-Ile | L-Leu |
| NT69L | | | | | | | | N-methyl-Arg | L-Lys | L-Pro | L-neo-Trp | tert-Leu | L-Leu |
| NT69L' | | | | | | | | N-methyl-Arg | L-Arg | L-Pro | L-neo-Trp | tert-Leu | L-Leu |
| NT71 | | | | | | | | N-methyl-Arg | DAB$^\S$ | L-Pro | L-neo-Trp | tert-Leu | L-Leu |
| NT72 | | | | | | | | | D-Lys | L-Pro | L-neo-Trp | tert-Leu | L-Leu |
| NT73 | | | | | | | | | D-Lys | L-Pro | L-neo-Trp | L-Ile | L-Leu |
| NT74 | | | | | | | | | DAB | L-Pro | L-neo-Trp | tert-Leu | L-Leu |
| NT75 | | | | | | | | | DAB | L-Pro | L-neo-Trp | L-lle | L-Leu |
| NT76 | | | | | | | | L-Arg | D-Orn | L-Pro | L-neo-Trp | L-Ile | L-Leu |
| NT77 | | | | | | | | L-Arg | D-Orn | L-Pro | L-neo-Trp | tert-Leu | L-Leu |

*Tsuchiya Y et al., (1989) European Patent Application 89104302.8;
$^\#$naphthalylalanine;
$^\S$diaminobutyric acid;
$^&$D-ornithine As used herein, a "polypeptide" is any chain of amino acid residues, regardless of post-translational modification (e.g., phosphorylation or glycosylation). Polypeptides of the invention typically are between 3 and 30 amino acids in length (e.g., 3, 4, 5, 6, 7, 8, 9, 10, 11, 12, 13, 14, 15, 20, 25, or 30 amino acids in length). For example, a polypeptide can be between 3 and 13 amino acids in length.

The term "amino acid" refers to natural amino acids, unnatural amino acids, and amino acid analogs, all in their D and L stereoisomers if their structures so allow. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr), and valine (Val). Unnatural amino acids include, without limitation, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4-diaminoisobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, N-methylisoleucine, N-methylvaline, norvaline, norleucine, ornithine, pipecolic acid, N-methylarginine and neo-tryptophan.

An "analog" is a chemical compound that is structurally similar to another but differs slightly in composition, as in the replacement of one atom by an atom of a different element, the presence of a particular functional group, or the replacement of an amino acid with another amino acid. An "amino acid analog" therefore is structurally similar to a naturally occurring amino acid molecule as is typically found in native polypeptides, but differs in composition such that either the C-terminal carboxy group, the N-terminal amino group, or the side-chain functional group has been chemically modified to another functional group. Amino acid analogs include natural and unnatural amino acids that are chemically blocked, reversibly or irreversibly, or modified on their N-terminal amino group or their side-chain groups, and include, for example, methionine sulfoxide, methionine sulfone, S-(carboxymethyl)-cysteine, S-(carboxymethyl) -cysteine sulfoxide, and S-(carboxymethyl)-cysteine sulfone. Amino acid analogs may be naturally occurring, or can be synthetically prepared. Non-limiting examples of amino acid analogs include aspartic acid-(beta-methyl ester), an analog of aspartic acid; N-ethylglycine, an analog of glycine; and alanine carboxamide, an analog of alanine. Other examples of amino acids and amino acids analogs are listed in Gross and Meienhofer, *The Peptides: Analysis, Synthesis, Biology*, Academic Press, Inc., New York (1983).

The stereochemistry of a polypeptide can be described in terms of the topochemical arrangement of the side chains of the amino acid residues about the polypeptide backbone, which is defined by the peptide bonds between the amino acid residues and the I-carbon atoms of the bonded residues. In addition, polypeptide backbones have distinct termini and thus direction. The majority of naturally occurring amino acids are L-amino acids. Naturally occurring polypeptides are largely comprised of L-amino acids. D-amino acids are the enantiomers of L-amino acids and can form "inverso" polypeptides (i.e., peptides corresponding to native peptides but made up of D-amino acids rather than L-amino acids).

Polypeptides can be modified for use in vivo by the addition, at the amino-or carboxy-terminal end, of a stabilizing agent to facilitate survival of the polypeptide in vivo. This can be useful in situations in which peptide termini tend to be degraded by proteases prior to cellular uptake. Such blocking agents can include, without limitation, additional related or unrelated amino acid sequences that can be attached to the amino- and/or carboxy-terminal residues of a polypeptide (e.g., an acetyl group attached to the N-terminal amino acid or an amide group attached to the C-terminal amino acid). Such attachment can be achieved either chemically, during the synthesis of the polypeptide, or by recombinant DNA technology using methods familiar to those of ordinary skill in the art. Alternatively, blocking agents such as pyroglutamic acid or other molecules known in the art can be attached to the amino- and/or carboxy-terminal residues, or the amino group at the amino terminus or the carboxy group at the carboxy terminus can be replaced with a different moiety.

Polypeptides also can contain an amino acid tag. A "tag" is generally a short amino acid sequence that provides a ready means of detection or purification through interactions with an antibody against the tag or through other compounds or molecules that recognize the tag. For example, tags such as c-myc, hemagglutinin, polyhistidine, or Flag® can be used to aid purification and detection of a polypeptide. As an example, a polypeptide with a polyhistidine tag can be purified based on the affinity of histidine residues for nickel ions (e.g., on a Ni-NTA column), and can be detected in western blots by an antibody against polyhistidine (e.g., the Penta-His antibody; Qiagen, Valencia, Calif.). Tags can be inserted anywhere within a polypeptide sequence, although insertion at the amino-or carboxy-terminus is particularly useful.

NTR agonists that can be used as described herein also can be peptidomimetic compounds designed on the basis of the amino acid sequences of NT polypeptides. Peptidomimetic compounds are synthetic, non-peptide compounds having a three-dimensional conformation (i.e., a "peptide motif") that is substantially the same as the three-dimensional conformation of a selected polypeptide, and thus can confer the same or similar function as the selected polypeptide. Peptidomimetic compounds can be designed to mimic any of the NT polypeptides provided herein.

Peptidomimetic compounds that are protease resistant are particularly useful. Furthermore, peptidomimetic compounds may have additional characteristics that enhance therapeutic effects, such as increased cell permeability and prolonged biological half-life. Such compounds typically have a backbone that is partially or completely non-peptide, but with side groups that are identical or similar to the side groups of the amino acid residues that occur in the polypeptide upon which the peptidomimetic compound is based. Several types of chemical bonds (e.g., ester, thioester, thioamide, retroamide, reduced carbonyl, dimethylene and ketomethylene) can be useful substitutes for peptide bonds in the construction of peptidomimetic compounds.

Polypeptides that can be used as described herein can be produced by a number of methods, many of which are well known in the art. By way of example and not limitation, a polypeptide can be obtained by extraction from a natural source (e.g., from isolated cells, tissues, or bodily fluids), by expression of a recombinant nucleic acid encoding the polypeptide (as, for example, described herein), or by chemical synthesis (e.g., by solid-phase synthesis or other methods well known in the art, including synthesis with an ABI peptide synthesizer; Applied Biosystems, Foster City, Calif.).

NT analogs such as NT69L can be synthesized using Fmoc chemistry with t-butyl-protected side chains on an automated peptide synthesizer, for example. See, U.S. Pat. No. 6,214,790 and Cusack et al. (2000) Brain Res. 856: 48–54. NT69L has the amino acid sequence N-methyl-Arg-Lys-Pro-L-neo-Trp-tert-Leu-Leu (SEQ ID NO:3). The L-neo-Trp residue can be synthesized by, for example, the method of Fauq et al. (Fauq et al. supra), or by methods disclosed in U.S. Pat. No. 6,214,790. Once synthesized, the polypeptide can be purified by, for example, HPLC (e.g., reverse phase HPLC).

NT polypeptides also can be prepared by recombinant technology using isolated nucleic acid molecules encoding the polypeptides. As used herein, "nucleic acid" refers to both RNA and DNA, including cDNA, genomic DNA, and synthetic (e.g., chemically synthesized) DNA. The nucleic acid can be double-stranded or single-stranded (i.e., a sense or an antisense single strand).

Nucleic acids encoding NT polypeptides can be contained within nucleic acid vectors. A vector is a replicon, such as a plasmid, phage, or cosmid, into which another nucleic acid segment may be inserted so as to bring about the replication of the inserted segment. Vectors that are useful to produce NT polypeptides typically are expression vectors, in which the nucleotides encode an NT polypeptide with an initiator methionine, operably linked to expression control sequences. As used herein, "operably linked" means incorporated into a genetic construct so that expression control sequences effectively control expression of a coding sequence of interest. An "expression control sequence" is a nucleic acid sequence that controls and regulates the transcription and translation of another nucleic acid sequence, and an "expression vector" is a vector that includes expression control sequences, so that a relevant nucleic acid segment incorporated into the vector is transcribed and translated. A coding sequence is "operably linked" and "under the control" of transcriptional and translational control sequences in a cell when a polymerase transcribes the coding sequence into mRNA, which then is translated into the polypeptide encoded by the coding sequence.

Methods well known to those skilled in the art may be used to subclone isolated nucleic acid molecules encoding NT polypeptides into expression vectors containing relevant coding sequences and appropriate transcriptional/translational control signals. See, for example, Sambrook et al., *Molecular Cloning: A Laboratory Manual* (2nd edition), Cold Spring Harbor Laboratory, New York (1989); and Ausuble et al., *Current Protocols in Molecular Biology*, Green Publishing Associates and Wiley Interscience, New York (1989). Expression vectors can be used to produce NT polypeptides in a variety of systems (e.g., bacteria, yeast, insect cells, and mammalian cells). Examples of suitable expression vectors include, without limitation, plasmids and viral vectors derived from herpes viruses, retroviruses, vaccinia viruses, adenoviruses, and adeno-associated viruses. A wide variety of expression vectors and systems are commercially available, including the pET series of bacterial expression vectors (Novagen, Madison, Wis.), the Adeno-X expression system (Clontech), the Baculogold baculovirus expression system (BD Biosciences Pharmingen, San Diego, Calif.), and the pCMV-Tag vectors (Stratagene, La Jolla, Calif.).

Expression systems that can be used for small or large scale production of NT polypeptides include, without limitation, microorganisms such as bacteria (e.g., *E. coli* and *B. subtilis*) transformed with recombinant bacteriophage DNA, plasmid DNA, or cosmid DNA expression vectors containing nucleic acid molecules encoding NT polypeptides; yeast (e.g., *S. cerevisiae*) transformed with recombinant yeast expression vectors containing nucleic acid molecules encoding NT polypeptides; insect cell systems infected with recombinant virus expression vectors (e.g., baculovirus) containing nucleic acid molecules encoding NT polypeptides; plant cell systems infected with recombinant virus expression vectors (e.g., tobacco mosaic virus) or transformed with recombinant plasmid expression vectors (e.g., Ti plasmid) containing nucleic acid molecules encoding NT polypeptides; or mammalian cell systems (e.g., primary cells or immortalized cell lines such as COS cells, CHO cells, HeLa cells, HEK 293 cells, and 3T3 L1 cells) harboring recombinant expression constructs containing promoters derived from the genome of mammalian cells (e.g., the metallothionein promoter) or from mammalian viruses (e.g., the adenovirus late promoter and the cytomegalovirus promoter), along with nucleic acid molecules encoding NT polypeptides.

The invention provides substantially pure NT polypeptides. The term "substantially pure" as used herein with reference to a polypeptide means the polypeptide is substantially separated from other molecules and compounds. Thus, a naturally occurring polypeptide that is substantially pure is substantially free of other polypeptides, lipids, carbohydrates, and nucleic acid with which it associates in nature. A non-naturally occurring polypeptide (e.g., a synthetic polypeptide or a peptidomimetic) that is substantially pure is substantially free of the chemical components included in the synthesis reaction. Typically, a substantially pure polypeptide will yield a single major band on a non-reducing polyacrylamide gel. A substantially pure NT polypeptide can be at least about 60 percent pure (e.g., at least about 65, 70, 75, 80, 85, 90, 95, or 99 percent pure). It is understood that an NT polypeptide is considered substantially pure if it has been purified and then mixed with, for example, an adjuvant or a pharmaceutical carrier, as the NT polypeptide is separated from the cellular components with which it is associated in nature and separated from the components with which it is associated in a synthesis reaction. Suitable methods for purifying NT polypeptides can include, for example, affinity chromatography, immunoprecipitation, size exclusion chromatography, and ion exchange chromatography. The extent of purification can be measured by any appropriate method, including but not limited to: column chromatography, polyacrylamide gel electrophoresis, or high-performance liquid chromatography.

Small molecules also can be used in the methods provided herein to reduce the effects of nicotine. Such small molecules (i.e., non-polypeptide NTR agonists) can be isolated and identified using assays such as ELISA and binding assays (e.g., affinity chromatography). For example, NTR molecules can be coated in the wells of a microtiter plate or coupled to a chromatography resin. Cellular extracts or solutions containing a cocktail of small molecules can be incubated in the wells or with the resin. Molecules that do not bind can be washed away, while bound molecules can be eluted by, for example, washing with a buffer containing a relatively high concentration of salt.

Compositions

NTR agonists can be incorporated into compositions that can be used to reduce nicotine effects. Any method for formulating and subsequently administering therapeutic compositions can be used. Dosing generally is dependent on the severity and responsiveness of the condition to be treated, with the course of treatment lasting from several days to several months, or until the condition (e.g., nicotine sensitization or addiction) is alleviated or diminished to an extent deemed satisfactory by the subject or a treating clinician. Optimum dosages can vary depending on the relative potency of individual NTR agonists, and generally can be estimated based on $EC_{50}$ found to be effective in in vitro and in vivo animal models. Typically, dosage is from 0.01 µg to 100 g per kg of body weight. Compositions containing NTR agonists can be given once or more daily, weekly, or even less often.

The methods provided herein include the administration of pharmaceutical compositions and formulations that include NTR agonists. NTR agonists therefore can be admixed, encapsulated, conjugated or otherwise associated with other molecules, molecular structures, or mixtures of molecules such as, for example, liposomes, receptor targeted molecules, or oral, rectal, topical or other formulations, for assisting in uptake, distribution and/or absorption.

A "pharmaceutically acceptable carrier" is a pharmaceutically acceptable solvent, suspending agent, or any other pharmacologically inert vehicle for delivering one or more therapeutic compounds (e.g., NT69L) to a subject. Pharmaceutically acceptable carriers can be liquid or solid, and can be selected with the planned manner of administration in mind so as to provide for the desired bulk, consistency, and other pertinent transport and chemical properties, when combined with one or more of therapeutic compounds and any other components of a given pharmaceutical composition. Typical pharmaceutically acceptable carriers include, by way of example and not limitation: water; saline solution; binding agents (e.g., polyvinylpyrrolidone or hydroxypropyl methylcellulose); fillers (e.g., lactose and other sugars, gelatin, or calcium sulfate); lubricants (e.g., starch, polyethylene glycol, or sodium acetate); disintegrates (e.g., starch or sodium starch glycolate); and wetting agents (e.g., sodium lauryl sulfate).

Pharmaceutical compositions can be administered by a number of methods. Administration can be, for example, topical (e.g., transdermal, ophthalmic, or intranasal); pulmonary (e.g., by inhalation or insufflation of powders or aerosols); oral; or parenteral (e.g., by subcutaneous, intrathecal, intraventricular, intramuscular, or intraperitoneal injection, or by intravenous drip). Administration can be rapid (e.g., by injection) or can occur over a period of time (e.g., by slow infusion or administration of slow release formulations). For treating tissues in the central nervous system, an NTR agonist can be administered by injection or infusion into the cerebrospinal fluid, preferably with one or more agents capable of promoting penetration of the agonist across the blood-brain barrier.

Formulations for topical administration of NTR agonists include, for example, sterile and non-sterile aqueous solutions, non-aqueous solutions in common solvents such as alcohols, or solutions in liquid or solid oil bases. Such solutions also can contain buffers, diluents and other suitable additives. Pharmaceutical compositions and formulations for topical administration can include transdermal patches, ointments, lotions, creams, gels, drops, suppositories, sprays, liquids, and powders. Conventional pharmaceutical carriers, aqueous, powder or oily bases, thickeners and the like may be necessary or desirable.

Compositions and formulations for oral administration of NTR agonists include, for example, powders or granules, suspensions or solutions in water or non-aqueous media, capsules, sachets, or tablets. Such compositions also can incorporate thickeners, flavoring agents, diluents, emulsifiers, dispersing aids, or binders.

Compositions and formulations for parenteral, intrathecal or intraventricular administration can include sterile aqueous solutions, which also can contain buffers, diluents and other suitable additives (e.g., penetration enhancers, carrier compounds and other pharmaceutically acceptable carriers).

Pharmaceutical compositions include, but are not limited to, solutions, emulsions, aqueous suspensions, and liposome-containing formulations. These compositions can be generated from a variety of components that include, for example, preformed liquids, self-emulsifying solids and self-emulsifying semisolids. Emulsions are often biphasic systems comprising of two immiscible liquid phases intimately mixed and dispersed with each other; in general, emulsions are either of the water-in-oil (w/o) or oil-in-water (o/w) variety. Emulsion formulations have been widely used for oral delivery of therapeutics due to their ease of formulation and efficacy of solubilization, absorption, and bioavailability.

Liposomes are vesicles that have a membrane formed from a lipophilic material and an aqueous interior that can contain the antisense composition to be delivered. Liposomes can be particularly useful due to their specificity and the duration of action they offer from the standpoint of drug delivery. Liposome compositions can be formed from phosphatidylcholine, dimyristoyl phosphatidylcholine, dipalmitoyl phosphatidylcholine, dimyristoyl phosphatidylglycerol, or dioleoyl phosphatidylethanolamine, for example. Numerous lipophilic agents are commercially available, including Lipofectin® (Invitrogen/Life Technologies, Carlsbad, Calif.) and Effectene™ (Qiagen, Valencia, Calif.).

Compositions containing NTR agonists can further encompass any pharmaceutically acceptable salts, esters, or salts of such esters, or any other compound which, upon administration to a mammal (e.g., a human), is capable of directly or indirectly providing the biologically active agonist or residue thereof. Accordingly, for example, the invention provides pharmaceutically acceptable salts of NTR agonists, prodrugs and pharmaceutically acceptable salts of such prodrugs, and other bioequivalents. A prodrug is a therapeutic agent that is prepared in an inactive form and is converted to an active form (i.e., drug) within the body or cells thereof by the action of endogenous enzymes or other chemicals and/or conditions. A pharmaceutically acceptable salt is a physiologically and pharmaceutically acceptable salt of an NTR agonist (i.e., a salt that retains the desired biological activity of the parent agonist molecule without imparting undesired toxicological effects). Examples of pharmaceutically acceptable salts include, but are not limited to, salts formed with cations (e.g., sodium, potassium, calcium, or polyamines such as spermine); acid addition salts formed with inorganic acids (e.g., hydrochloric acid, hydrobromic acid, sulfuric acid, phosphoric acid, or nitric acid); salts formed with organic acids (e.g., acetic acid, citric acid, oxalic acid, palmitic acid, or fumaric acid); and salts formed from elemental anions (e.g., chlorine, bromine, and iodine).

Pharmaceutical compositions containing NTR agonists also can incorporate penetration enhancers that promote the efficient delivery of polypeptides and small molecules to the skin of animals. Penetration enhancers can enhance the diffusion of both lipophilic and non-lipophilic drugs across cell membranes. Penetration enhancers can be classified as belonging to one of five broad categories, i.e., surfactants (e.g., sodium lauryl sulfate, polyoxyethylene-9-lauryl ether and polyoxyethylene-20-cetyl ether); fatty acids (e.g., oleic acid, lauric acid, myristic acid, palmitic acid, and stearic acid); bile salts (e.g., cholic acid, dehydrocholic acid, and deoxycholic acid); chelating agents (e.g., disodium ethylenediaminetetraacetate, citric acid, and salicylates); and non-chelating non-surfactants (e.g., unsaturated cyclic ureas).

Compositions can contain other adjunct components conventionally found in pharmaceutical compositions. Thus, the compositions also can include compatible, pharmaceutically active materials such as, for example, antipruritics, astringents, local anesthetics or anti-inflammatory agents, or additional materials useful in physically formulating various dosage forms of the compositions of the present invention, such as dyes, flavoring agents, preservatives, antioxidants, opacifiers, thickening agents and stabilizers. Furthermore, the composition can be mixed with auxiliary agents, e.g., lubricants, preservatives, stabilizers, wetting agents, emulsifiers, salts for influencing osmotic pressure, buffers, colorings, flavorings, and aromatic substances. When added, however, such materials should not unduly interfere with the biological activities of the NTR agonists within the compositions. The formulations can be mixed with auxiliary agents (e.g., lubricants, preservatives, stabilizers, wetting agents, emulsifiers, salts for influencing osmotic pressure, buffers, colorings, flavorings and/or aromatic substances and the like) that do not deleteriously interact with the agonist(s) of the formulation.

Pharmaceutical formulations can be presented conveniently in unit dosage form, and can be prepared according to conventional techniques well known in the pharmaceutical industry. Such techniques include the step of bringing into association the active ingredients (e.g., NT69L) with the desired pharmaceutical carrier(s). Typically, a formulation can be prepared by uniformly and bringing the active ingredients into intimate association with liquid carriers or finely divided solid carriers or both, and then, if necessary, shaping the product. Formulations can be sterilized if desired, provided that the method of sterilization does not interfere with the effectiveness of the NTR agonist(s) contained in the formulation.

Compositions containing NTR agonists can be formulated into any of many possible dosage forms such as, but not limited to, tablets, capsules, liquid syrups, soft gels, suppositories, and enemas. Compositions also can be formulated as suspensions in aqueous, non-aqueous or mixed media. Aqueous suspensions further can contain substances that increase the viscosity of the suspension including, for example, sodium carboxymethylcellulose, sorbitol, and/or dextran. Suspensions also can contain stabilizers.

Compositions containing NTR agonists also can contain one or more smoking cessation compounds. The term "smoking cessation compound" as used herein refers to compounds that are used to help mammals overcome an addiction to nicotine caused by, for example, prolonged use of cigarettes or other tobacco products. Such compounds can include nicotine (typically in lower doses than found in a cigarette) and anti-depressants such as bupropion. Compositions that can be used as described herein can contain an NTR agonist, a smoking cessation compound, and a pharmaceutically acceptable carrier. For example, a patch or pill can be designed to contain NT69L and nicotine or bupropion.

Methods for Reducing Nicotine Effects

Animals that are naïve to nicotine exhibit an initial depression in motor activity upon administration of nicotine, followed by an increase in activity. Repeated nicotine administration results in tolerance to the depressant effect and sensitization to the stimulant effects of nicotine. Thus, constant doses of nicotine produce increasing degrees of locomotor activity after repeated administration.

The invention provides methods for using NTR agonists and compositions containing NTR agonists to treat the effects of nicotine. The effects of nicotine include, for example, hyperactivity, gastrointestinal distress, hypothermia, respiratory distress, hypertension, tachycardia, increased gastrointestinal motility, prolactin release, sensitization, dependence, and addiction. In some embodiments, one or more NTR agonists, or a composition containing one or more NTR agonists in combination with one or more smoking cessation compounds, can be administered to a mammal (e.g., a rat, a mouse, a dog, or a human) such that an effect of nicotine is reduced or blocked. Nicotine effects can include pharmacological and psychological elements such as, for example, hyperactivity, sensitization, and addiction. One or more NTR agonists can be administered to a mammal using any suitable method, including those described herein. The alleviation of nicotine effects after treatment with an NTR agonist (e.g., NT69L) can be monitored by, for example, decreased locomotor activity or reduced craving for nicotine.

The invention will be further described in the following examples, which do not limit the scope of the invention described in the claims.

EXAMPLES

Example 1

Materials and Methods

NT69L synthesis: NT69L was synthesized as described by Cusack et al., supra. NT69L has the following sequence: (N-methyl-Arg-Lys-Pro-L-neo-Trp-tert-Leu-Leu; SEQ ID NO:3). Briefly, polypeptides were synthesized using Fmoc chemistry with t-butyl-protected side chains, on automated peptide synthesizers (Applied Biosystems model 431 A, Foster City, Calif.). Protocols concerning activation, coupling times, amino acid dissolution, coupling solvents, and synthesis scale were carried out according to standard methods. All peptides were purified by reverse-phase HPLC using a C18 column (2.2×25 cm, Vydac, Hesperia, Calif.) in 0.1% trifluoroacetic acid (TFA)/water and a gradient of 10% –60% acetonitrile in 0.1% TFA/water. A combination of analytical HPLC and mass spectrometry (PE Sciex 1 56B, Foster City, Calif.) was used to analyze peptide purity. NT69L was dissolved in saline for i.p. administration.

Animals and treatment protocol: Male Sprague-Dawley rats weighing 200–250 g were housed in a temperature-controlled room with free access to food and water under artificial 12 hour light/dark cycle. All tests were conducted during the light cycle. The animals received an intraperitoneal (i.p.) injection of either NT69L (1 mg/kg) or an equivalent volume (100 µl) of saline. Thirty minutes after the first injection, the rats received subcutaneous (s.c.) injections of saline or nicotine (0.35 mg/kg). These injections were repeated once a day for 15 days. On days 1 and 15, rats were placed in a Plexiglass Opto-Varimax Minor motility chamber (Columbus Instruments, Columbus, Ohio) and allowed to acclimate for one hour. Baseline activity was recorded for 30 minutes for each rat. The rats then were injected with either saline or NT69L and replaced in the chamber. After 30 minutes, each rat was injected with either saline or nicotine and returned to the chamber. Activity was recorded for 60 minutes. After testing for locomotor activity on day 15, animals were sacrificed. Brain sections were dissected on ice and maintained on dry ice until they were frozen at −80° C., at which temperature they were stored until being assayed. [$^3$H] cytisine binding: Nicotinic receptor binding sites in membrane homogenates of frozen tissue were measured using [$^3$H] cytisine according to the method of Pabreza et al. [(1991) Mol. Pharmacol. 39:9–12]. Frozen tissue was resuspended in 50 mM Tris-HCl buffer (pH 7.4), homogenized with a Brinkmann Polytron (setting 6), and washed twice in fresh Tris buffer by centrifugation at 35000×g. The resulting pellets were resuspended in buffer. Aliquots of homogenates were added to tubes containing [$^3$H] cytisine in the presence or absence of 100 μM nicotine and incubated in a final volume of 250 μl for 75 minutes at 4° C. The binding reactions were terminated by filtration through GF/B filter paper that was mounted on a Brandel cell harvester. Filters were presoaked in 0.5% polyethylenimine to reduce binding of radioligand to the filter. The filters were washed 3 times with cold 0.9% NaCl and counted in a scintillation counter. The data were analyzed using the PC version of the ligand software program. Specific binding was defined as the difference between binding in the presence and absence of 100 μM nicotine.

Dopamine D2 receptor binding assay: Homogenized brain tissue was assayed for dopamine D2 receptor binding by the method of Bowden et al. [(1997) Brain Res. 752: 227–233]. Briefly, brain tissue was homogenized in buffer (50 mM Tris-HCl, 5 mM KCl and 120 mM NaCl, pH 7.5) and centrifuged at 26,000×g for 10 minutes at 4° C. Pellets were resuspended in buffer to 1 mg/10 μl and immediately used for binding. Aliquots of 20 pl tissue homogenates were added to 25 PI [$^3$H] raclopride and 25 μl buffer (for total binding) or 25 μl of 30 nM sulipride (for nonspecific binding) in a total volume of 250 μl, and incubated at room temperature for 90 minutes. Membrane-bound radioactivity was recovered by filtration under vacuum through Whatman GF/B filters using a Brandel cell harvester. Filters were washed with ice-cold PBS and radioactivity was determined by liquid scintillation counting. Protein levels were quantified using the Micro BCA assay (Pierce, Rockford, Ill.).

Striatal dopamine: Brain dopamine levels were analyzed using high performance liquid chromatography with electrochemical detection (HPLC-EC, ESA, Inc., Chemsford, Mass.), according to previously described procedures (Kilts et al. (1981) J. Chromatogr. 225:347–357; and Krstulovic (1982) J. Chromatogr. 229:1–34). Rats were sacrificed by decapitation, brains were removed, and the striatal tissue was weighed and homogenized in 10 volumes of ice-cold 0.1 N perchloric acid containing 10 mM EDTA. Tissue homogenates were centrifuged at 26,000×g for 10 minutes at 4° C. A 20 μl aliquot of the diluted supernatant was injected onto an HPLC system with an MD-150/RP-C18 column (ESA). The mobile phase contained 10% acetonitrile with 75 mM sodium dihydrogen phosphate, 1.7 mM 1-octane sulfonic acid sodium salt, 0.01% triethylamine, and 25 μM EDTA, pH 3.0. The flow rate was maintained at 0.5 ml/minute. The detector potentials were set at: 350 mV; E1:−175 mV and E2:250 mV. The concentration of dopamine in each sample was quantified by comparison of area under curve (AUC) between samples and external standards run on the same day.

Statistical analysis: Statistical analyses were carried out by one way analysis of variance (ANOVA) followed by Tukey's test for multiple comparisons, using Sigma Stat software, with P<0.05 being considered significant. Graphs were generated with the use of GraphPad Software (San Diego, Calif.).

Example 2

Nicotine-induced Hyperactivity

Sprague Dawley rats were divided into seven groups and injected daily for 14 days with the treatment listed outside the parentheses under each pair of columns in FIG. 1. On day 15, the rats were injected with the treatment listed inside the parentheses under each pair of columns. Locomotor activity was recorded on days 1 and 15. Rats were placed in a motility chamber for one hour for acclimation. A 30 minute baseline was recorded for each rat. The rats were injected with either saline or NT69L and placed in the chamber for 30 minutes. Each rat was then removed from the chamber, injected with either nicotine or saline, and returned to the chamber. Activity was recorded for 60 minutes, and is shown in counts per 10 minute interval.

As depicted in FIG. 1, a single injection of nicotine significantly increased the peak level of locomotor activity as compared to the control group [sal/nic(sal/nic) vs. sal/sal (sal/sal); P<0.001]. Acute injection of NT69L on day 1, 30 minutes prior to nicotine injection, reduced nicotine-induced hyperactivity by 24% [sal/nic(69/nic) vs. 69/nic(69/nic); P<0.001]. The reduction in activity was not due to sedation, as there was no significant difference between the 69/sal and the sal/sal groups on day 1. Rats receiving daily nicotine injections responded with more than a 60% increase in peak activity, indicating sensitization to the stimulant effects of nicotine [sal/nic(sal/nic); day 1 vs. day 15]. This effect was markedly reduced (to 10% of control) by a single injection of NT69L given 30 minutes prior to nicotine on the fifteenth day of nicotine administration [sal/nic(sal/nic) vs. sal/nic (69/nic); P<0.001]. Daily injection of NT69L reduced the magnitude of locomotor sensitization by 24%. Nonetheless, a statistically significant reduction in activity, compared with saline, was observed after fifteen days of treatment with NT69L [sal/nic(sal/nic) vs. 69/nic(69/nic); P<0.05].

Example 3

Cytisine Binding

Sprague Dawley rats were maintained and treated as described above. Animals were sacrificed on day 15 after being tested for locomotor activity. PFC and VTA sections were harvested on ice and frozen at −80° C until being assayed for cytisine binding as described in Example 1.

Figure 2:
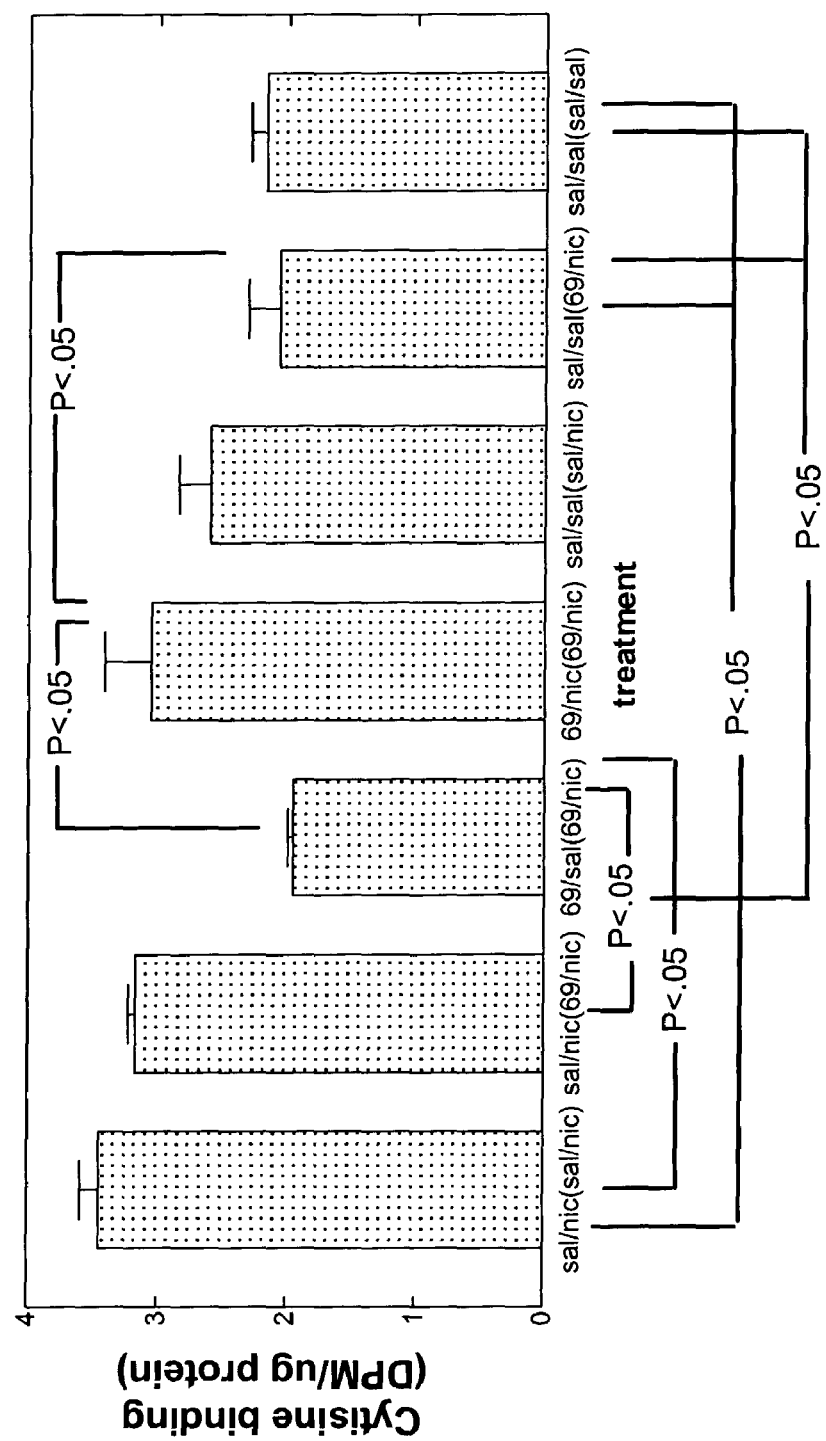
FIG. 2 is a bar graph showing the effects of NT69L and/or nicotine on cytisine binding in the prefrontal cortex (PFC).

The effect of acute nicotine injection on cytisine binding to the PFC and VTA was assessed by comparing the sal/sal (sal/nic) group to the sal/sal(sal/sal) group. A single nicotine injection on day 15 tended to increase cytisine binding in the PFC, but not to a significant level (FIG. 2). Fifteen daily injections of nicotine, however, increased cytisine binding in prefrontal cortex by 62% when compared to cytisine binding in the saline control group [sal/nic(sal/nic) vs. sal/sal(sal/ sal); P<0.05]. Cytisine binding in rats treated with NT69L also was increased after 15 days of nicotine injection [sal/ nic(69/nic) vs. sal/sal(69/nic)]. Injection of NT69L daily for 15 days significantly reduced (62%) cytisine binding caused by acute, but not by chronic, nicotine injections [69/sal(69/ nic) vs. 69/nic(69/nic)]. In addition, acute injection of NT69L prior to nicotine injection on day fifteen reduced the increase caused by 15 daily injections of nicotine by 65% [sal/nic(69/nic) vs. sal/sal(69/nic)].

Figure 3:
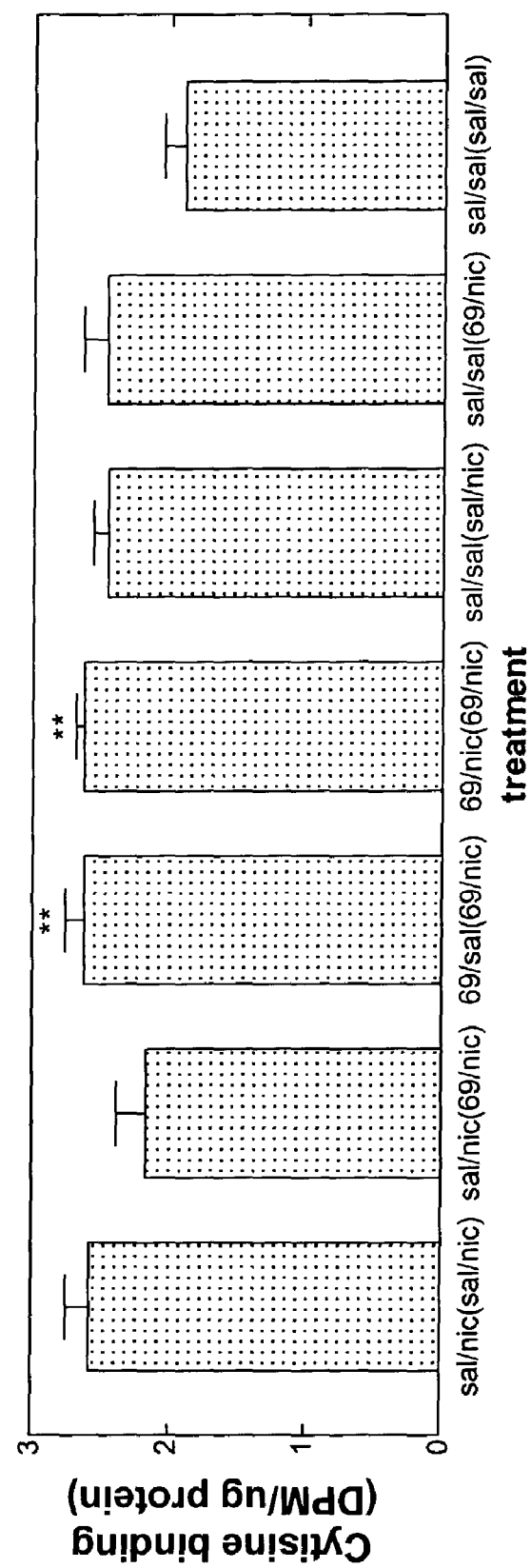
FIG. 3 is a bar graph showing the effects of NT69L and/or nicotine on cytisine binding in the ventral tegmental area (VTA). ** $P<0.05$ vs. sal/sal(sal/sal).

Nicotine and NT69L resulted in a 35% increase in cytisine binding in the VTA as compared to saline control, although only chronic injection of NT69L was significant [FIG. 3; 69/sal(69/nic) and 69/nic(69/nic) vs. sat/sal(sal/sal); $P<0.05$]. Because there was not a good correlation between nicotinic receptor binding and the reduction of nicotine's effects by NT69L in either brain area, the data suggest that the effects of NT69L are mediated by sites other than nicotinic receptors.

Example 4

Dopamine and Metabolites

Sprague Dawley rats were treated as described above. Animals were sacrificed on day 15 after being tested for locomotor activity. Striatal and PFC tissues were harvested on ice and frozen at −80° C. until being assayed for dopamine metabolism as detailed in Example 1.

Figure 4:
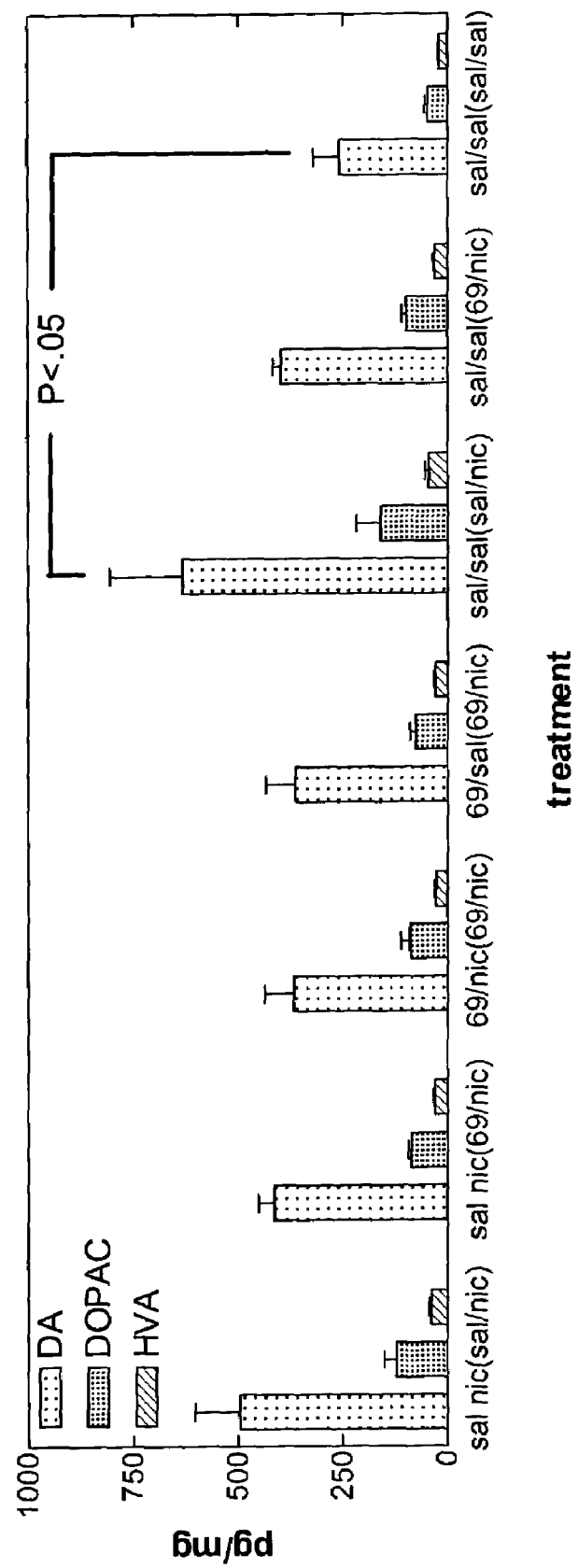
FIG. 4 is a bar graph showing the effects of nicotine and/or NT69L on dopamine and its metabolites in rat striatum. DA, dopamine; DOPAC, 3,4-dihydroxyphenylacetic acid; HVA, homovanillic acid.

As depicted in FIG. 4, a single injection of nicotine resulted in a 192% increase in striatal dopamine levels [sal/sal(sal/nic) vs. sal/sal(sal/sal); $P<0.05$]. Pretreatment with NT69L did not significantly affect dopamine levels in the striatum.

Figure 5:
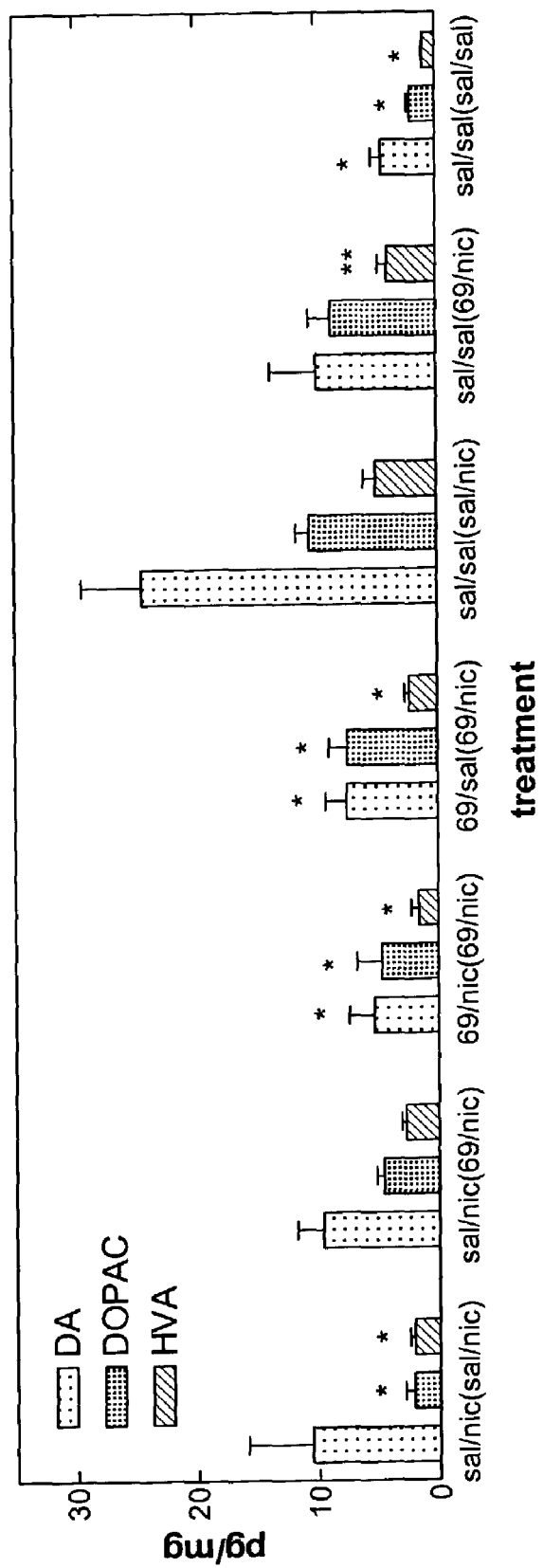
FIG. 5 is a bar graph showing the effects of nicotine and/or NT69L on dopamine and its metabolites in the PFC. * significantly different from sal/sal(sal/nic); ** $P<0.05$ vs. sal/sal(sal/sal).

In the PFC, a single injection of nicotine resulted in a 400% increase in levels of dopamine and its metabolites, as determined by HPLC-ECD [FIG. 5; sal/sal(sal/nic) vs. sal/sal(sal/sal); $P<0.05$]. Fifteen daily injections of nicotine reduced this effect to 232% as compared to saline control [sal/sal(sal/sal) vs. sal/nic(sal/nic)]. Injection of NT69L for 15 days or pretreating rats with NT69L before nicotine injection on day 15 lowered the nicotine-induced increase in dopamine by 62% and 28% respectively [69/nic(69/nic) and 69/sal(69/nic) vs. sal/sal(sal/nic)].

Dopamine (D2) receptor binding in striatum was higher in saline-treated animals than in any other group. No difference, however, was seen across any of the nicotine and NT69L treatment groups. These results suggest that the effects of NT69L on nicotine-induced hyperactivity are mediated by a reduction of nicotine-induced DA release, without an effect on the number of dopamine D2 binding sites.

Example 5

Norepinephrine

Sprague Dawley rats were treated as described above. Animals were sacrificed on day 15 after being tested for locomotor activity. PFC sections were harvested on ice and frozen at −80° C. until being assayed for norepinephrine levels.

Figure 6:
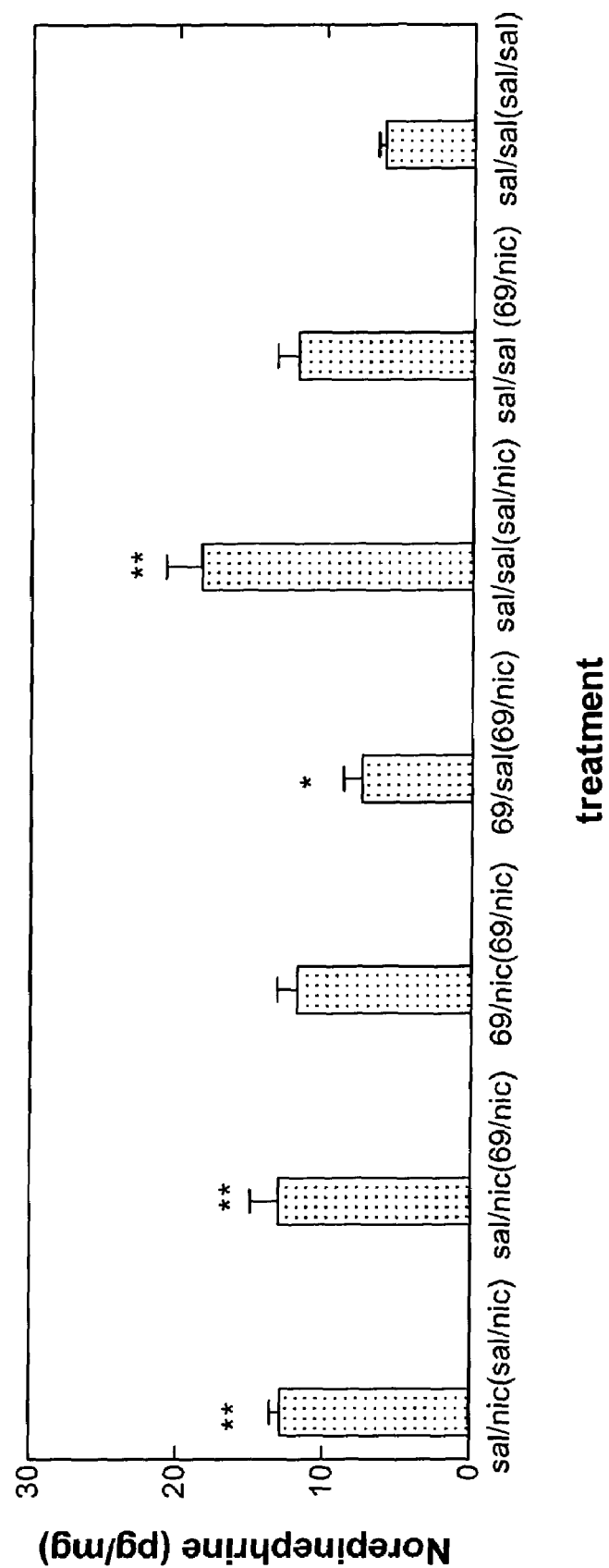
FIG. 6 is a bar graph showing the effects of nicotine and/or NT69L on norepinephrine levels in the PFC. * significantly different from sal/sal(sal/nic); ** $P<0.05$ vs. sal/sal(sal/sal).

As shown in FIG. 6, acute and chronic treatment with nicotine significantly increased norepinephrine levels in the PFC by 213–300% as compared to saline control [sal/nic (sal/nic), sal/nic(69/nic) and sal/sal(sal/nic) vs. sal/sal(sal/sal); $P<0.05$]. Daily injections of NT69L blocked the increase caused by a single injection of nicotine, resulting in a 40% reduction in norpeinephrine levels [69/sal(69/nic) vs. sal/sal(sal/nic)]. No significant differences were observed in the striatum between treatment groups. These results suggest that norepinephrine may be involved in sensitization to nicotine, since only chronic treatment with NT69L reduced the increase in norepinephrine release.

Example 6

NT69L Inhibition of Nicotine Sensitization

For a longer term study of nicotine sensitization, rats were divided into seven groups that were treated once a week for six weeks with saline or NT69L followed by a challenge with saline or 0.35 mg/kg nicotine. These experiments allowed examination of both the initiation and expression phases of sensitization. Group 1 received saline/saline each week. Group 2 received saline/saline for the first five weekly treatments, and saline/nicotine in the sixth week. Group 3 received saline/nicotine each week. Group 4 received NT69L/saline each week. Group 5 received NT69L/nicotine each week. Group 6 received NT69L/nicotine for the first five weekly treatments, and saline/nicotine in the sixth week. Group 7 received saline/nicotine for the first five weekly treatments, and NT69L/nicotine in the sixth week. Locomotor activity was measured after each weekly treatment, as described in Example 1.

Figure 7:
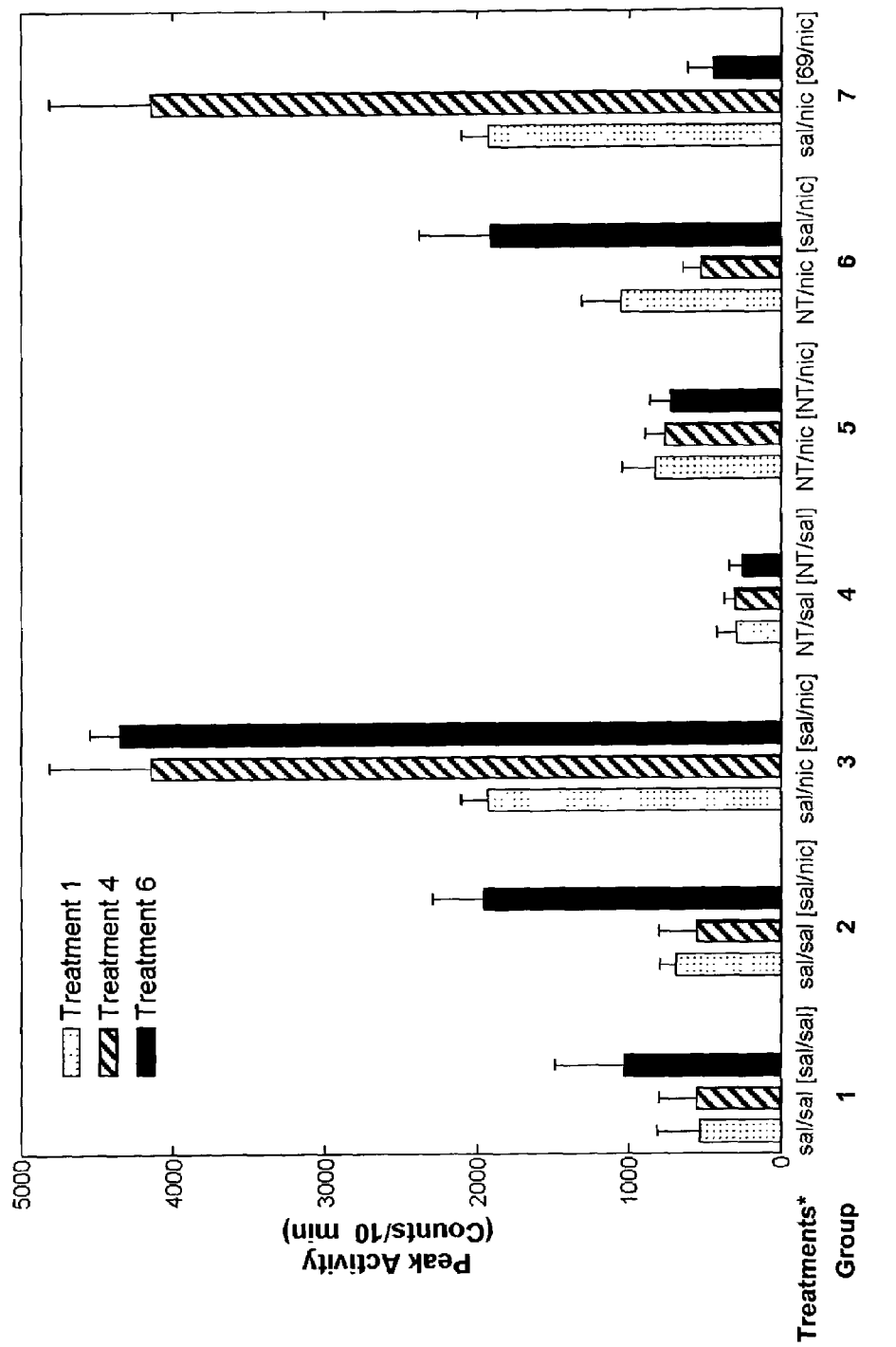
FIG. 7 is a bar graph showing the effects of weekly treatment with NT69L and/or nicotine on nicotine-induced locomotor activity in rats.

FIG. 7 depicts average activity levels for each group of animals after treatments 1, 4 and 6. Nicotine challenge in the sixth week only, without NT69L treatment, resulted in hyperactivity (group 2). Nicotine challenge each week in the absence of NT69L treatment resulted in increased activity, but sensitization occurred by the fourth week so that a further increase in activity was not observed after the sixth challenge (group 3). Treatment with NT69L before nicotine challenge largely prevented the hyperactivity (group 5), whereas the removal of NT69L treatment in the sixth week resulted in nicotine-induced activity at the level similar to that seen in other groups upon first exposure to nicotine in the absence of NT69L (group 6, third column as compared to group 2, third column, group 3, first column, and group 7, first column). Nicotine challenge for five weeks without NT69L treatment resulted in hyperactivity, but treatment with NT69L in the sixth week resulted in a significant decrease in activity (group 7). The NT69L neurotensin agonist therefore effectively blocked both the initiation of nicotine sensitization (i.e., as evidenced by the lack of sensitization in week 6 for group 6) and the expression of nicotine sensitization (i.e., as evidenced by the reduction in hyperactivity after five weekly doses of nicotine).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for reducing a nicotine effect in a mammal pre-exposed to nicotine, said method comprising administering a neurotensin receptor agonist to said mammal in an amount effective to reduce said nicotine effect, wherein said neurotensin receptor agonist is a polypeptide consisting of the sequence set forth in SEQ ID NO:3.

2. The method of claim 1, wherein said administering is by injection.

3. The method of claim 1, wherein said polypeptide is administered in combination with a phannaceutically acceptable carrier.

* * * * *

UNITED STATES PATENT AND TRADEMARK OFFICE
CERTIFICATE OF CORRECTION

PATENT NO. : 7,087,575 B2
APPLICATION NO. : 10/198697
DATED : August 8, 2006
INVENTOR(S) : Elliott Richelson, Paul Fredrickson, and Mona Boules It is certified that error appears in the above-identified patent and that said Letters Patent is hereby corrected as shown below:

Title Page, Title, please delete "Effect" and insert --Effects--therefor;

Title Page, References Cited, Other Publications, second Cusack et al. reference, please delete "Pharmacolgical" and insert --Pharmacological--therefor;

Title Page (Page 2), References Cited, Other Publications, please insert

--Cusack et al., "Effects of a novel neurotensin peptide analog given extracranially on CNS behaviors mediated by apomorphine and haloperidol," Brain. Res., 2000, 856:48-54--;

Title Page (Page 2), References Cited, Other Publications, second Fredrickson et al. reference, please delete "pf" and insert --of--therefor;

Title Page (Page 2), References Cited, Other Publications, Hedley et al. reference, please delete "Agonsit" and insert --Agonist--therefor;

Title Page (Page 2), References Cited, Other Publications, first Hertel et al. reference, please delete "Repeated administration" and insert --Induction of tolerance to the suppressant effect--therefor;

Title Page (Page 2), References Cited, Other Publications, Huang and Hanson reference, please delete "Differntial" and insert --Differential--therefor;

Title Page (Page 2), References Cited, Other Publications, Jolicocur and Barbeau reference, please delete "Jolicocur" and insert --Jolicoeur--therefor;

Title Page (Page 2), References Cited, Other Publications, Kilts et al. reference, please delete "Chromotography" and insert --Chromatography--therefor;

Title Page (Page 2), References Cited, Other Publications, Li et al. reference, please delete "postynapic" and insert --postsynaptic--therefor;

Title Page (Page 2), References Cited, Other Publications, Morbeck et al. reference, please delete "if" and insert --of--therefor;

Title Page (Page 2), References Cited, Other Publications, Morbeck et al. reference, please delete "fo" and insert --of--therefor;

UNITED STATES PATENT AND TRADEMARK OFFICE
CERTIFICATE OF CORRECTION

PATENT NO. : 7,087,575 B2
APPLICATION NO. : 10/198697
DATED : August 8, 2006
INVENTOR(S) : Elliott Richelson, Paul Frederickson, and Mona Boules It is certified that error appears in the above-identified patent and that said Letters Patent is hereby corrected as shown below:

Title Page (Page 2), References Cited, Other Publications, Radke et al. reference, please delete "termina" and insert --terminal-- therefor;

Column 18, line 39, please delete "phannaceutically" and insert --pharmaceutically-- therefor.

Signed and Sealed this

Twenty-eighth Day of November, 2006

JON W. DUDAS
*Director of the United States Patent and Trademark Office*